(12) United States Patent
Howard et al.

(10) Patent No.: US 7,528,126 B2
(45) Date of Patent: May 5, 2009

(54) PYRROLOBENZODIAZEPINES

(75) Inventors: Philip Wilson Howard, St Albans (GB); Stephen John Gregson, London (GB); Peter William Taylor, London (GB); David Edwin Thurston, Fareham (GB); Tsveta Stefanova Hadjivassileva, Pontypridd (GB)

(73) Assignee: Spirogen Limited, Isle of Wight ( * ) Notice: Subject to any disclaimer, the term of this patent is extended or adjusted under 35 U.S.C. 154(b) by 0 days.

(21) Appl. No.: 10/598,691

(22) PCT Filed: Mar. 9, 2005

(86) PCT No.: PCT/GB2005/000915
§ 371 (c)(1), (2), (4) Date: Feb. 14, 2007

(87) PCT Pub. No.: WO2005/085260
PCT Pub. Date: Sep. 15, 2005

(65) Prior Publication Data
US 2007/0185073 A1    Aug. 9, 2007

(30) Foreign Application Priority Data
Mar. 9, 2004 (GB) ................... 0405319.5
Jun. 3, 2004 (GB) ................... 0412409.5

(51) Int. Cl.
C07D 519/00 (2006.01)
A61K 31/5517 (2006.01)

(52) U.S. Cl. ...................... 514/220; 540/498

(58) Field of Classification Search ............. 540/498; 514/220
See application file for complete search history.

(56) References Cited

U.S. PATENT DOCUMENTS

| | | | |
|---|---|---|---|
| 3,523,941 A | 8/1970 | Leimgruber et al. | |
| 3,524,849 A | 8/1970 | Batcho et al. | |
| 4,185,016 A | 1/1980 | Takanabe et al. | |
| 4,239,683 A | 12/1980 | Takanabe et al. | |
| 4,309,437 A | 1/1982 | Ueda et al. | |
| 5,418,241 A | 5/1995 | Jegham et al. | |
| 6,562,806 B1 | 5/2003 | Thurston et al. | |
| 6,608,192 B1 | 8/2003 | Thurston et al. | |
| 6,660,856 B2 | 12/2003 | Wang | |
| 6,747,144 B1 | 6/2004 | Thurston et al. | |
| 7,049,311 B1 | 5/2006 | Thurston et al. | |
| 7,067,511 B2 | 6/2006 | Thurston et al. | |
| 7,265,105 B2 | 9/2007 | Thurston et al. | |
| 7,407,951 B2 | 8/2008 | Thurston et al. | |
| 2003/0195196 A1 | 10/2003 | Thurston et al. | |
| 2004/0092736 A1 | 5/2004 | Thurston et al. | |
| 2004/0198722 A1 | 10/2004 | Thurston et al. | |
| 2006/0264622 A1 | 11/2006 | Howard et al. | |
| 2007/0173497 A1 | 7/2007 | Howard et al. | |
| 2007/0191309 A1 | 8/2007 | Howard et al. | |
| 2007/0191349 A1 | 8/2007 | Howard et al. | |
| 2008/0167293 A1 | 7/2008 | Howard et al. | |

FOREIGN PATENT DOCUMENTS

| | | |
|---|---|---|
| EP | 1193270 | 4/2002 |
| FR | 2027356 | 12/1969 |
| FR | 2586683 | 3/1987 |
| GB | 1299198 | 12/1972 |
| JP | 53-82792 | 7/1978 |
| JP | 57131791 | 8/1982 |
| JP | 58180487 | 10/1983 |
| WO | WO 92/19620 | 11/1992 |
| WO | WO 93/18045 | 9/1993 |
| WO | 00/12506 | 3/2000 |
| WO | 00/12509 | 3/2000 |

(Continued)

OTHER PUBLICATIONS

Abb, J., "In vitro activity of linezolid, quinupristin-dalfopristin, vancymycin, teicoplanin, moxifloxacin and mupirocin against methicillin-resistant *Staphylococcus aureus*: comparative evaluation by the E test and a broth microdilution method," Diag. Microb. Inf. Disease (2002) 43:319-321.

Adams et al., "Molecular modelling of a sequence-specific DNA-binding agent based on the pyrrolo[2,1-c][1,4]benzodiazepines," Pharm. Pharmacol. Commun. (1999) 5:555-560.

(Continued)

*Primary Examiner*—Bruck Kifle
(74) *Attorney, Agent, or Firm*—Michael Best & Friedrich LLP

(57) ABSTRACT

A compound of formula (I) and salts and solvates thereof, wherein: $R^{10}$ is a nitrogen protecting group and $R^{11}$ is either OH or O—$R^{12}$, wherein $R^{12}$ is an oxygen protecting group, or $R^{10}$ and $R^{11}$ together form a double bond between N10 and C11; and $R^{10'}$ and $R^{11'}$ are selected from the same options as $R^{10}$ and $R^{11}$ respectively.

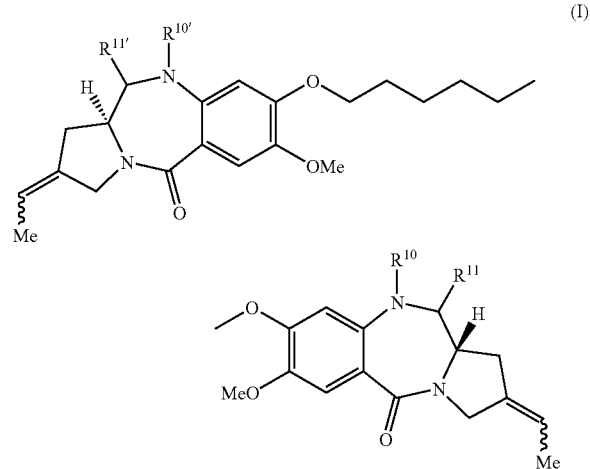

9 Claims, 2 Drawing Sheets

FOREIGN PATENT DOCUMENTS

| | | |
|---|---|---|
| WO | WO 00/12507 | 3/2000 |
| WO | WO 00/12508 | 3/2000 |
| WO | WO 2004/043963 | 5/2004 |
| WO | WO 2005/023814 | 3/2005 |
| WO | 2005/042535 | 5/2005 |
| WO | WO 2005/040170 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | 2005/110423 | 11/2005 |

OTHER PUBLICATIONS

Arima et al., "Studies on Tomaymycin, a New Antibiotic. I. Isolation and Properties of Tomaymycin," *J. Antibiotics* (1972) 25:437-444.

Baba, T. et al., "Genome and virulence determinants of high virulence community-acquired MRSA," Lancet (2002) 359:1819-1827.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," *Tetrahedron Letters* (2000) 41:6171-6174.

Bose et al., "New Approaches to Pyrrolo[2,1-c][1,4]benzodiazepines: Synthesis, DNA-binding and cytotoxicity of DC-81," *Tetrahedron*, 48, 751-758 (1992).

Bose, D.S. et al., "Rational Design of a Highly Efficient Irreversible DNA Interstrand Cross-Linking Agent Based on the Pyrrolobenzodiazepine Ring System," *J. Am. Chem. Soc.*, 114, 4939-4941 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", *Tetrahedron Letters*, vol. 34, No. 33, 5327-28 (1993).

Enright, M.C., "The evolution of a resistant pathogen—the case of MRSA," Curr. Opin. Pharmac. (2003) 3:474-479.

Farmer, J.D. et al., "DNA binding properties of a new class of linked anthramycin analogs,", *Chemical Abstracts*, Abstract No. 239940r, vol. 114, No. 25, 25 899-903 (1991).

Foloppe, M.P. et al., "DNA-binding properties of pyrrolo[2,1-c][1,4]benzodiazephine N10-C11 amidines," *Eur. J. Med. Chem.*, 31, 407-410 (1996).

Fujisawa Pharmaceutical Co., Ltd., Abstract No. 139983k, "Benzodiazepine derivatives", *Chemical Abstracts*, vol. 99, No. 17, 603 (1983).

Fujisawa Pharmaceutical Co., Ltd., Abstract No. 72145x, "Benzodiazepine derivatives", *Chemical Abstracts*, vol. 98, No. 9, 638 (1983).

Fujisawa Pharmaceutical Co. Ltd., "Benzodiazepine derivatives," *SciFinder Scholar*, 2-3 (2002).

Fukuyama, T. et al., "Total Synthesis of (+)-Porothramycin B," *Tetrahedron Letters*, vol. 34, 16, 2577-2580 (1993).

Greene, T.W. and Wuts, P.G.M., *Protective Groups in Organic Synthesis*, John Wiley & Sons, 2nd ed., Ch 7, 315-345 (1991).

Gregson, S. et al., "Synthesis of a novel C2/C2'-exo unsaturated pyrrolobenzodiazepine cross-linking agent with remarkable DNA binding affinity and cytotoxicity," *Chemical Communications*, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).

Gregson, S.J. et al., "Effect of C2-*exo* Unsaturation on the Cytotoxicity and DNA-Binding Reactivity of Pyrrolo[2,1-c]1,4]benzodiazepines", *Bioorganic & Medicinal Chemistry Letters*, 10: 1845-1847 (2000).

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Guiotto, A. et al., "Synthesis of novel C7-aryl substituted pyrrolo[2,1-c][1,4]benzodiazepines (PBDs) via Pro-N10-troc protection and suzuki coupling," *Bioorganic & Medicinal Chemistry Letters*, 8, No. 21, 3017-3018 (1998).

Hara et al., "DC 102, a new glycosidic pyrrolo(1,4)benzodiazepine antibiotic produced by *Streptomyces* sp.", *J. Antibiotics*, 41, 702-704 (1988).

Hartley, J.A. et al., "An agarose gel method for the determination of DNA interstrand crosslinking applicable to the measurement of the rate of total and 'second arm' crosslink reactions," Anal. Biochem. (1991) 193:131-134.

Hiramatsu, K. et al., "The emergence of *Staphylococcus aureus* with reduced susceptibility to vancomycin in Japan," Am. J. Med. (1998) 104(5A):7S-10S.

Hochlowski, J. et al., "Abbeymycin, a new anthramycin-type antibiotic produced by a streptomycete," *J. Antibiotics*, 40, 145-148 (1987).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *Micromonospora* sp." *J. Antibiotics*, 41, 1281-1284 (1988).

Kamal, A., et al., "An Efficient Synthesis of Pyrrolo[2,1-c][1,4] Benzodiazepine Antibiotics via Reductive Cyclization," *Bioorg. Med. Chem. Ltrs*, 7, No. 14, 1825-1828 (1997).

Kamal, A., et al., "Synthesis of Pyrrolo [2,1-c][1,4]-Benzodiazepine Antibiotics: Oxidation of Cyclic Secondary Amine with TPAP", *Tetrahedron*, v. 53, No. 9, 3223-3230 (1997).

Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kunimoto et al., "Mazethramycin, a new member of anthramycin group antibiotics," *J. Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," J. Am. Chem. Soc., 110, 2992-2993 (1988).

Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).

Leimgruber, W. et al., "Total synthesis of anthramycin," J. Am. Chem. Soc., 90, 5641-5643 (1968).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomamycin adduct," J. Med. Chem. (1994) 37:3132-3140.

Munoz Bellido, J.L. et al., "In vitro activity of linezolid, synercid and telithromcin against genetically defined high level of fluoroquinolone-resistant methicillin-resistant Staphylococcus aureus," Int. J. Antimicr. Agents (2002) 20:61-64.

Nagasaka, T. and Koseki, Y, "Stereoselective Synthesis of Tilivalline," Journal of Organic Chemistry, vol. 63, No. 20, 6797-6801 (1998).

Nagasaka, T. et al., "Stereoselective Synthesis of Tilivalline," Tetrahedron Letters, 30:14, 1871-1872 (1989).

O'Neil, I.A., et al., "The Synthesis of Functionalized Pyrrolo-[2,1-c][1,4]-Benzodiazepines," Synlett, 75-78 (1997).

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).

O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).

Quirk, M., "First VRSA isolate identified in USA," The Lancet (2002) 2:510.

Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).

Shimizu, K et al., "Prothracarcin, a Novel Antitumor Antibiotic," J. Antibiotics, 35, 972-978 (1982).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Suggs, J.W. et al., "Synthesis and structure of anthramycin analogs via hydride reduction of dilactams," Tetrahedron Letters, 26, No. 40, 4871-4874 (1985).

Takeuchi, T. et al., "Neothramycins A and B, New Antitumor Antibiotics," J. Antibiotics, 29, 93-96 (1976).

Tercel, M. et al., "Unsymmetrical DNA cross-linking agents: combination of the CBI and PBD pharmacophores," J. Med. Chem. (2003) 46:2132-2151.

Thurston, D.E. and Thompson, A.S., "The molecular recognition of DNA," Chem. Brit., 26, 767-772 (1990).

Thurston, D.E. and Bose, D.S., "Synthesis of DNA-Interactive Pyrrolo[2,1-c][1,4]benzodiazepines," Chem. Rev., 94:433-465 (1994).

Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).

Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

Tsunakawa, M. et al., "Porothramycin, a new antibiotic of the anthramycin group: Production, isolation, structure and biological activity," J. Antibiotics, 41:1366-1373 (1988).

Umezawa, H. et al., Chemical Abstract No. 4427a, "Mazethramycins" Chemical Abstracts, vol. 90, No. 1, 428 (1979).

Umezawa, H. et al., "Mazethramycins," SciFinder Scholar, 2-3 (2002).

Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42:4028-4041 (1999).

Farmer, J.D. et al., "Synthesis and DNA crosslinking ability of a dimeric anthramycin analog," Tetrahedron Letters (1988) 29(40):5105-5108, Abstract only.

Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.

Weidner-Wells, M.A. et al., "Photochemical approach to the synthesis of the pyrrolo[1,4]benzodiazepine antibiotics," J. Org. Chem. (1989) 54:5746-5758.

PYRROLOBENZODIAZEPINES

CROSS-REFERENCE TO RELATED APPLICATIONS

This patent application is a national stage filing under 35 U.S.C. 371 of International Application No. PCT/GB2005/000915, filed on Mar. 9, 2005, which claims foreign priority benefits to United Kingdom Application No. 0405319.5, filed Mar. 9, 2004 and United Kingdom Application No. 0412409.5, filed Jun. 3, 2004.

The present invention relates to a specific pyrrolobenzodiazepine (PBD) dimer with C2-exo unsaturation.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

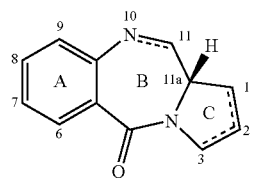

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, *In Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

In WO 93/18045, some of the present inventors disclosed the following compound (Example 6):

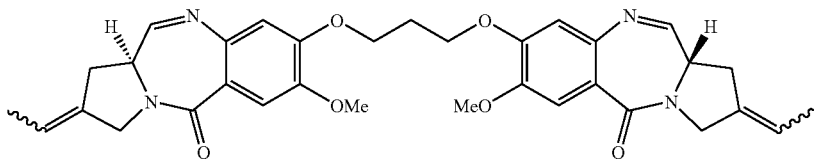

The final compound produced was a mixture of the E-, E-form, the Z-, Z-form and the E-, Z-forms as a result of the synthesis method used. Extrapolating from the last compound for which the amount of different geometric isomers was measured, the final compound would likely have the following proportions of geometric isomers:

| Geometric isomers at C2/C2' | Amount (%) |
|---|---|
| E-, E- | 42 |
| E-, Z- | 46 |
| Z-, Z- | 12 |

Gram-Positive Bacteria

Infectious diseases are a leading cause of mortality and morbidity worldwide. Our ability to treat effectively a range of bacterial infections rose dramatically following the introduction of penicillin and other antibiotics, but multi-drug resistance has emerged as a serious threat to efforts to continue to keep infectious diseases under control.

Two of the most serious pathogens associated with drug resistance are methicillin resistant *Staphylococcus aureus* (MRSA) and vancomycin resistant enterococci (VRE).

MRSA has become one of the most problematic pathogens in humans not only in nosocomial but also recently in community-acquired infections (Tadashi Baba, et al., *The Lancet*, 359, 1819-1827 (2002); Enright, M. C., *Current Opinion in Pharmacology*, 3, 1-6 (2003)). *S. aureus* harmlessly colonises the nasal cavity of some 30-40% of the population and may also survive on dry skin for example on the hands. Health care workers and hospital staff may be carriers and may unwittingly infect patients under their care. *S. aureus*, an opportunistic pathogen, is of concern in immunocompromised people, prone to infection. It may infect many sites postoperatively if contaminated surgery equipment is used on, for example, open wounds. Blood, heart, bones and joints are also prime tissue-targets of infection. Furthermore toxic shock syndrome, pneumonia and food-poisoning contribute to the wide-spectrum of pathogenicity this organism causes. *S. aureus* infections had been treated successfully with potent antibiotics in the past, however the emergence of multi-drug resistance has limited opportunities to successfully treat these infections.

VRE account for nosocomial infections and is currently a major problem of many healthcare institutions. Although there are several members in the *Enterococcus* family, only two are usually associated with the high morbidity and mortality in hospitals, namely *E. faecalis* and *E. faecium*. Enterococci are part of the normal gastrointestinal tract flora and are carried by healthy individuals. Although many hospital patients may be colonised with VRE, this does not necessarily lead to infection. VRE infections tend to occur in immunocompromised and seriously ill patients such as those in intensive care units. It has been difficult to establish exactly how much VRE contributes to mortality rates as there are usually many other concomitant infections present in infected patients. In many cases, severe underlying diseases in patients are likely to be the sole cause of death not linked to VRE. The tissues affected are usually the urinary tract, surgical sites, blood and abdominal sites. In addition, endocarditis is a serious infection resulting as a consequence of VRE bacteraemia. The mode of transmission of VRE is similar to that of MRSA. Direct skin-to skin contact with colonised health care workers and contaminated surgical equipment seem to be the leading factors. It appears that the bacteria not only survive on the hands and arms of health workers but may also remain on bed linen and hospital beds as well as other surrounding objects for several days.

DISCLOSURE OF THE INVENTION

In a first aspect, the invention comprises a compound of formula I:

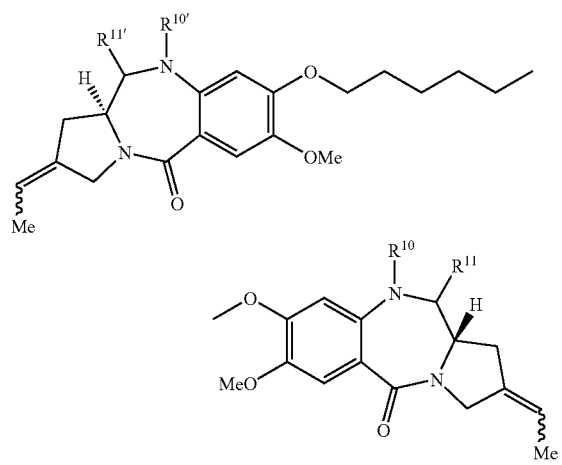

and salts and solvates thereof, wherein:
$R^{10}$ is a nitrogen protecting group and $R^{11}$ is either OH or O—$R^{12}$, wherein $R^{12}$ is an oxygen protecting group, or $R^{10}$ and $R^{11}$ together form a double bond between N10 and C11; and $R^{10'}$ and $R^{11'}$ are selected from the same options as $R^{10}$ and $R^{11}$ respectively.

It is preferred that $R^{10'}$ and $R^{11'}$ are the same as $R^{10}$ and $R^{11}$ respectively.

In a second aspect, the invention comprises the synthesis of a compound of formula I.

In a third aspect, the invention comprises a compound of formula I and pharmaceutically acceptable salts and solvates thereof, for use in a method of therapy.

In a fourth aspect, the invention comprises a pharmaceutical composition comprising a compound of formula I and pharmaceutically acceptable salts and solvates thereof, and a pharmaceutically acceptable excipient.

In a fifth aspect, the invention comprises the use of a compound of formula I and pharmaceutically acceptable salts and solvates thereof, in the manufacture of a medicament for the treatment of a gene-based disease.

In a sixth aspect, the invention comprises a method for the treatment of a gene-based disease, comprising administering to a subject suffering from a gene-based disease a therapeutically-effective amount of a compound of formula I or pharmaceutically acceptable salts and solvates thereof.

Definitions

Nitrogen Protecting Groups

Nitrogen protecting groups are well known in the art. Preferred nitrogen protecting groups are carbamate protecting groups that have the general formula:

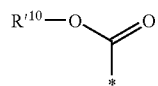

A large number of possible carbamate nitrogen protecting groups are listed on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Particularly preferred protecting groups include Alloc, Troc, Teoc, BOC, Doc, Hoc, TcBOC, Fmoc, 1-Adoc and 2-Adoc.

Also suitable for use in the present invention are nitrogen protecting groups which can be removed in vivo (e.g. enzymatically, using light) as described in WO 00/12507, which is incorporated herein by reference. Examples of these protecting groups include:

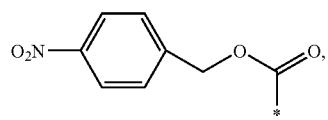

which is nitroreductase labile (e.g. using ADEPT/GDEPT);

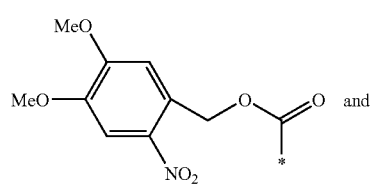

and

-continued

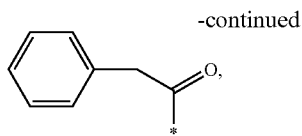

which are photolabile; and

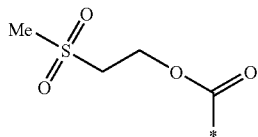

which is glutathione labile (e.g. using NPEPT).

Oxygen Protecting Groups

Oxygen protecting groups are well known in the art. A large number of suitable groups are described on pages 23 to 200 of Greene, T. W. and Wuts, G. M., Protective Groups in Organic Synthesis, 3$^{rd}$ Edition, John Wiley & Sons, Inc., 1999, which is incorporated herein by reference.

Classes of particular interest include silyl ethers, methyl ethers, alkyl ethers, benzyl ethers, esters, benzoates, carbonates, and sulfonates.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-7}$ Alkenyl: The term "$C_{2-7}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-7}$ alkynyl: The term "$C_{2-7}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —$CH_2$—C≡CH).

$C_{3-7}$ cycloalkyl: The term "$C_{3-7}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds: norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

N$_2$O$_1$: oxadiazine (C$_6$);
O$_1$S$_1$: oxathiole (C$_5$) and oxathiane (thioxane) (C$_6$); and,
N$_1$O$_1$S$_1$: oxathiazine (C$_6$).

Examples of substituted monocyclic heterocyclyl groups include those derived from saccharides, in cyclic form, for example, furanoses (C$_5$), such as arabinofuranose, lyxofuranose, ribofuranose, and xylofuranse, and pyranoses (C$_6$), such as allopyranose, altropyranose, glucopyranose, mannopyranose, gulopyranose, idopyranose, galactopyranose, and talopyranose.

C$_{5-20}$ aryl: The term "C$_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. C$_{3-20}$, C$_{5-7}$, C$_{5-6}$, etc.) denote the number of ring atoms, or range of number of ring atoms, whether carbon atoms or heteroatoms. For example, the term "C$_{5-6}$ aryl" as used herein, pertains to an aryl group having 5 or 6 ring atoms.

The ring atoms may be all carbon atoms, as in "carboaryl groups". Examples of carboaryl groups include, but are not limited to, those derived from benzene (i.e. phenyl) (C$_6$), naphthalene (C$_{10}$), azulene (C$_{10}$), anthracene (C$_{14}$), phenanthrene (C$_{14}$), naphthacene (C$_{18}$), and pyrene (C$_{16}$).

Examples of aryl groups which comprise fused rings, at least one of which is an aromatic ring, include, but are not limited to, groups derived from indane (e.g. 2,3-dihydro-1H-indene) (C$_9$), indene (C$_9$), isoindene (C$_9$), tetraline (1,2,3,4-tetrahydronaphthalene (C$_{10}$), acenaphthene (C$_{12}$), fluorene (C$_{13}$), phenalene (C$_{13}$), acephenanthrene (C$_{15}$), and aceanthrene (C$_{16}$).

Alternatively, the ring atoms may include one or more heteroatoms, as in "heteroaryl groups". Examples of monocyclic heteroaryl groups include, but are not limited to, those derived from:

N$_1$: pyrrole (azole) (C$_5$), pyridine (azine) (C$_6$);
O$_1$: furan (oxole) (C$_5$);
S$_1$: thiophene (thiole) (C$_5$);
N$_1$O$_1$: oxazole (C$_5$), isoxazole (C$_5$), isoxazine (C$_6$);
N$_2$O$_1$: oxadiazole (furazan) (C$_5$);
N$_3$O$_1$: oxatriazole (C$_5$);
N$_1$S$_1$: thiazole (C$_5$), isothiazole (C$_5$);
N$_2$: imidazole (1,3-diazole) (C$_5$), pyrazole (1,2-diazole) (C$_5$), pyridazine (1,2-diazine) (C$_6$), pyrimidine (1,3-diazine) (C$_6$) (e.g., cytosine, thymine, uracil), pyrazine (1,4-diazine) (C$_6$);
N$_3$: triazole (C$_5$), triazine (C$_6$); and,
N$_4$: tetrazole (C$_5$).

Examples of heteroaryl which comprise fused rings, include, but are not limited to:

C$_9$ (with 2 fused rings) derived from benzofuran (O$_1$), isobenzofuran (O$_1$), indole (N$_1$), isoindole (N$_1$), indolizine (N$_1$), indoline (N$_1$), isoindoline (N$_1$), purine (N$_4$) (e.g., adenine, guanine), benzimidazole (N$_2$), indazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S$_1$), benzothiazole (N$_1$S$_1$), benzothiadiazole (N$_2$S);

C$_{10}$ (with 2 fused rings) derived from chromene (O$_1$), isochromene (O$_1$), chroman (O$_1$), isochroman (O$_1$), benzodioxan (O$_2$), quinoline (N$_1$), isoquinoline (N$_1$), quinolizine (N$_1$), benzoxazine (N$_1$O$_1$), benzodiazine (N$_2$), pyridopyridine (N$_2$), quinoxaline (N$_2$), quinazoline (N$_2$), cinnoline (N$_2$), phthalazine (N$_2$), naphthyridine (N$_2$), pteridine (N$_4$);

C$_{11}$ (with 2 fused rings) derived from benzodiazepine (N$_2$);

C$_{13}$ (with 3 fused rings) derived from carbazole (N$_1$), dibenzofuran (O$_1$), dibenzothiophene (S$_1$), carboline (N$_2$), perimidine (N$_2$), pyridoindole (N$_2$); and, C$_{14}$ (with 3 fused rings) derived from acridine (N$_1$), xanthene (O$_1$), thioxanthene (S$_1$), oxanthrene (O$_2$), phenoxathiin (O$_1$S$_1$), phenazine (N$_2$), phenoxazine (N$_1$O$_1$), phenothiazine (N$_1$S$_1$), thianthrene (S$_2$), phenanthridine (N$_1$), phenanthroline (N$_2$), phenazine (N$_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a C$_{1-7}$ alkyl group (also referred to as a C$_{1-7}$ alkoxy group, discussed below), a C$_{3-20}$ heterocyclyl group (also referred to as a C$_{3-20}$ heterocyclyloxy group), or a C$_{5-20}$ aryl group (also referred to as a C$_{5-20}$ aryloxy group), preferably a C$_{1-7}$ alkyl group.

Alkoxy: —OR, wherein R is an alkyl group, for example, a C$_{1-7}$ alkyl group. Examples of C$_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a C$_{1-7}$ alkyl group, a C$_{3-20}$ heterocyclyl group, or a C$_{5-20}$ aryl group, preferably a C$_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$ alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O) Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

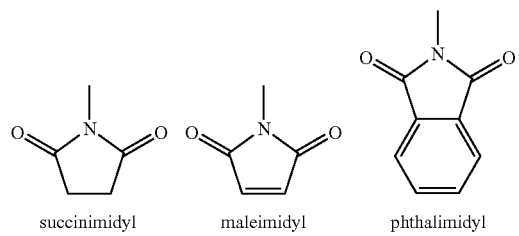

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

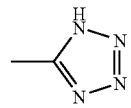

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)$CH_3$ and —S(=O)$CH_2CH_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2CH_3$ (methanesulfonyl, mesyl), —S(=O)$_2CF_3$ (triflyl), —S(=O)$_2CH_2CH_3$ (esyl), —S(=O)$_2C_4F_9$ (nonaflyl), —S(=O)$_2CH_2CF_3$ (tresyl), —S(=O)$_2CH_2CH_2NH_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —$SO_2H$.
Sulfonic acid (sulfo): —S(=O)$_2$OH, —$SO_3H$.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)$OCH_3$ (methoxysulfinyl; methyl sulfinate) and —S(=O)$OCH_2CH_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2OCH_3$ (methoxysulfonyl; methyl sulfonate) and —S(=O)$_2OCH_2CH_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)$CH_3$ and —OS(=O)$CH_2CH_3$.

Sulfonyloxy: —OS(=O)$_2$R, wherein R is a sulfonyloxy substituent, for example, a $C_{1-7}$ alkyl group, a $C_{3-20}$ heterocyclyl group, or a $CO_{520}$ aryl group, preferably a $C_{1-7}$ alkyl group. Examples of sulfonyloxy groups include, but are not limited to, —OS(=O)$_2CH_3$ (mesylate) and —OS(=O)$_2CH_2CH_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$alkyl group. Examples of sulfate groups include, but are not limited to, —OS(=O)$_2OCH_3$ and —SO(=O)$_2OCH_2CH_3$.

Sulfamyl (sulfamoyl; sulfinic acid amide; sulfinamide): —S(=O)$NR^1R^2$, wherein $R^1$ and $R^2$ are independently amino substituents, as defined for amino groups. Examples of sulfamyl groups include, but are not limited to, —S(=O)$NH_2$, —S(=O)NH($CH_3$), —S(=O)N($CH_3$)$_2$, —S(=O)NH($CH_2CH_3$), —S(=O)N($CH_2CH_3$)$_2$, and —S(=O)NHPh.

Sulfonamido (sulfinamoyl; sulfonic acid amide; sulfonamide): —S(=O)$_2NR^1R^2$, wherein $R^1$ and $R^2$ are independently amino substituents, as defined for amino groups. Examples of sulfonamido groups include, but are not limited to, —S(=O)$_2NH_2$, —S(=O)$_2NH(CH_3)$, —S(=O)$_2N(CH_3)_2$, —S(=O)$_2NH(CH_2CH_3)$, —S(=O)$_2N(CH_2CH_3)_2$, and —S(=O)$_2NHPh$.

Sulfamino: —$NR^1$S(=O)$_2$OH, wherein $R^1$ is an amino substituent, as defined for amino groups. Examples of sulfamino groups include, but are not limited to, —NHS(=O)$_2$OH and —N($CH_3$)S(=O)$_2$OH.

Sulfonamino: —$NR^1$S(=O)$_2$R, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2CH_3$ and —N($CH_3$)S(=O)$_2$$C_6H_5$.

Sulfinamino: —$NR^1$S(=O)R, wherein $R^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)$CH_3$ and —N($CH_3$)S(=O)$C_6H_5$.

Phosphino (phosphine): —$PR_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —$PH_2$, —P($CH_3$)$_2$, —P($CH_2CH_3$)$_2$, —P(t-Bu)$_2$, and —P(Ph)$_2$.

Phospho: —P(=O)$_2$.

Phosphinyl (phosphine oxide): —P(=O)$R_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)($CH_3$)$_2$, —P(=O)($CH_2CH_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)($OCH_3$)$_2$, —P(=O)($OCH_2CH_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)($OCH_3$)$_2$, —OP(=O)($OCH_2CH_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP($OCH_3$)$_2$, —OP($OCH_2CH_3$)$_2$, —(O-t-Bu)$_2$, and —OP(OPh)$_2$.

Phosphoramidite: —OP($OR^1$)—$NR^2_2$, where $R^1$ and $R^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP($OCH_2CH_3$)—N($CH_3$)$_2$, —OP($OCH_2CH_3$)—N(i-Pr)$_2$, and —OP($OCH_2CH_2CN$)—N(i-Pr)$_2$.

Phosphoramidate: —OP(=O)(OR$^1$)—NR$^2{}_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Gene-Based Diseases

Gene-based diseases include, and are preferably, proliferative diseases, and also include Alzheimer's disease and bacterial, parasitic and viral infections. Any condition which may be treated by the regulation of gene expression may be treated the compounds of the present invention.

Infection by gram-positive bacteria, and especially, MRSA and VRE, are particular preferred gene-based diseases in the present invention.

Proliferative Diseases

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Infection by Gram-Positive Bacteria

Gram-positive bacteria have been discussed above. The treatment of methicillin resistant *Staphylococcus aureus* (MRSA) and vancomycin resistant enterococci (VRE) are of particular interest, but the treatment of infection by other gram-positive bacteria, such as *Streptococcus pyogenes*, *Streptococcus agalactiae* and *Listeria monocytogenes* are also of interest.

Methods of Treatment

As described above, the present invention provides the use of a compound of formula I in a method of therapy. Preferably the compounds of formula I for use in therapy comprise two N10-C11 imine bonds, or the N10s are protected by nitrogen protecting groups (R$^{10}$, R$^{10'}$) which can be removed in vivo and the C11 substituents (R$^{11}$, R$^{11'}$) are OH. Also provided is a method of treatment, comprising administering to a subject in need of treatment a therapeutically-effective amount of a compound of formula I, preferably in the form of a pharmaceutical composition, which is the third aspect of the present invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy. If the compound of formula I bears a carbamate-based nitrogen protecting group which may be removed in vivo, then the methods of treatment described in WO 00/12507 (ADEPT, GDEPT and PDT) may be used.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms;

syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of the present invention have the following stereochemistry at the C11 position:

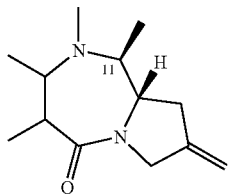

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

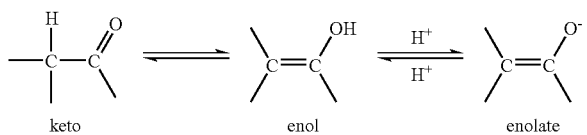

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g.—COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

A particular salt form of interest can be formed from compounds of formula I, where R$^{10}$ and R$^{11}$ (and/or R$^{10'}$ and R$^{11'}$) form an imine bond, by reacting said compound with a bisulphite salt to form a bisulphite derivative of the PBD. These compounds can be represented as:

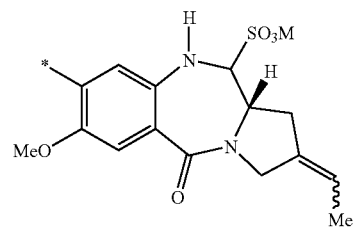

where M is a monovalent pharmaceutically acceptable cation, or if both PBDs are of these form, both Ms together form may a divalent pharmaceutically acceptable cation.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Solvates of particular relevance to the present invention are those where the solvent adds across the imine bond of the PBD, which is illustrated below where the solvent is water or an alcohol (R$^A$OH, where R$^A$ is an ether substituent as described above):

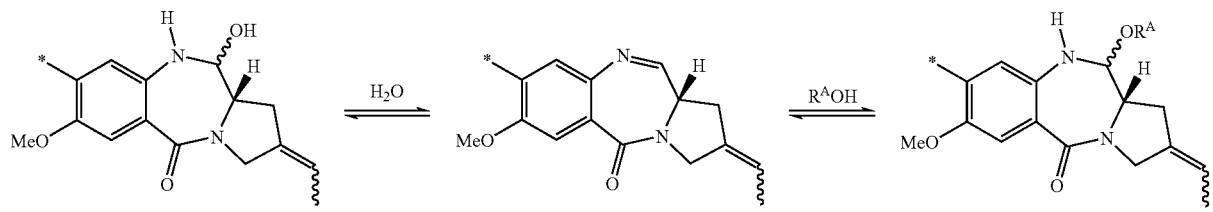

wherein, * indicates the dimer bridge (—O—(CH$_2$)$_5$—O—) to the corresponding PBD unit.

These forms can be called the carbinolamine and carbinolamine ether forms of the PBD. The balance of these equilibria depend on the conditions in which the compounds are found, as well as the nature of the moiety itself.

In general any nucleophilic solvent is capable of forming such solvates as illustrated above for hydoxylic solvents. Other nucleophilic solvents include thiols and amines.

These solvates may be isolated in solid form, for example, by lyophilisation.

GENERAL SYNTHETIC ROUTES

Figure 1:
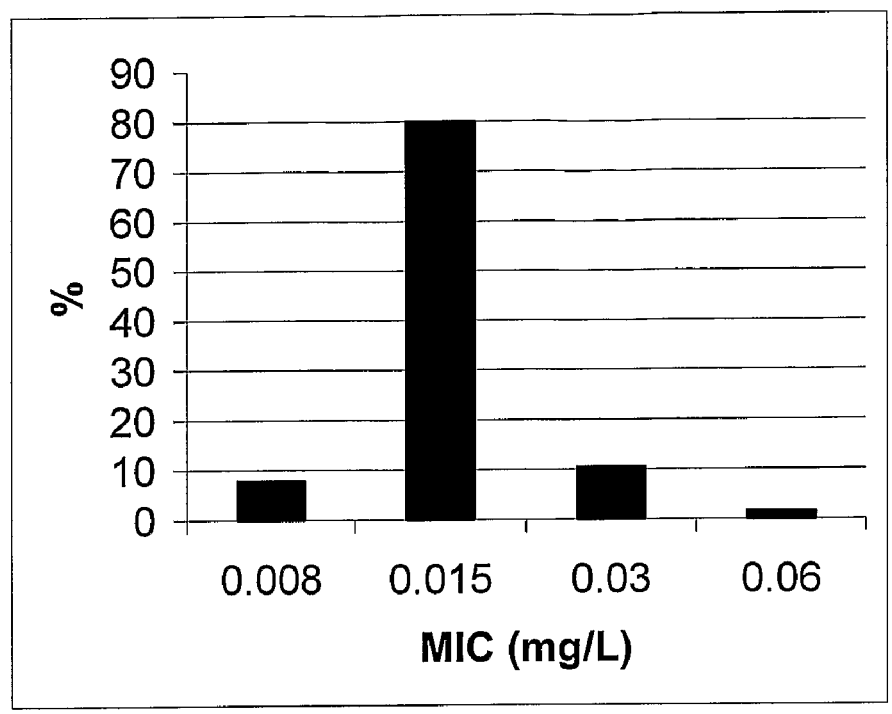
FIG. 1 shows the distribution of MICs of different MRSA strains for compound 1.

The compounds of formula I may be made by two alternative routes which are similar to those described in WO 00/12508. An important step is the formation of the C2-exo double bond. This may proceed by the methods described in schemes 8 and 9 of WO 00/12508.

One method involves the synthesis of the compound to provide the C-ring before coupling to the remainder of the molecule.

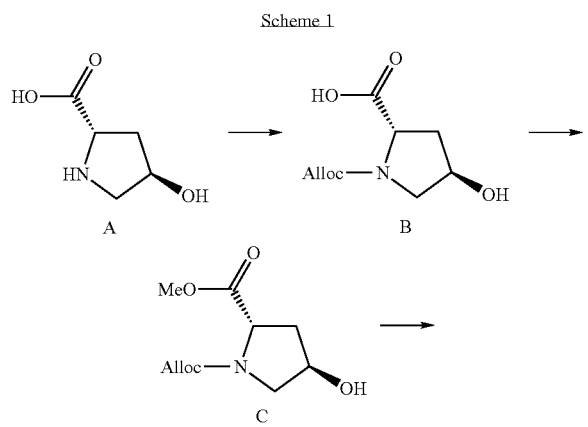

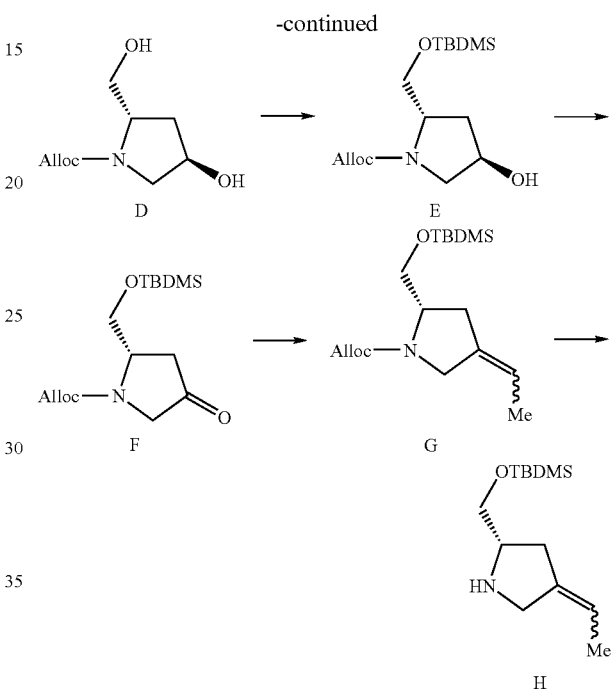

Commercially available trans-4-hydroxy-L-proline A can be N-alloc protected (or with any other suitable nitrogen protecting group) to give the protected compound B which can then be esterified using standard conditions. Hydride reduction of the ester C furnishes the diol D. Selective TBDMS protection of the diol gives a silyl ether E, which can then be oxidised, using, for example, Swern or TPAP oxidation, to provide the ketone F.

The C2-ethylidene functionality way be introduced by performing the Wittig reaction on ketone F. Palladium-mediated cleavage of the N-alloc protecting group yields compound H.

The compound H may then be joined to the A-ring dimer as follows:

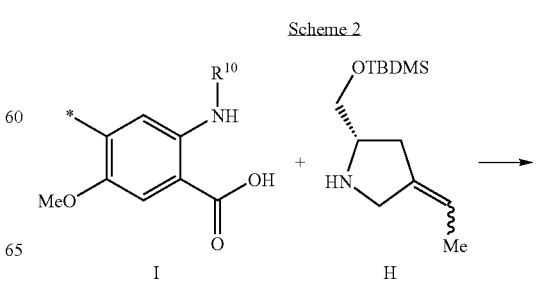

-continued

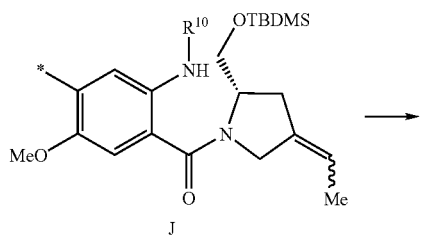
J

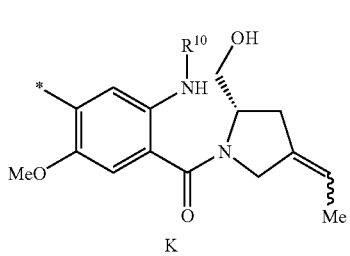
K

As shown in Scheme 2, the compound H is coupled (in 2 equivalents) to the N-troc protected anthranilic acid dimer I, where * indicates the dimer bridge (—O—(CH$_2$)$_5$—O—) to the corresponding PBD unit. This coupling is followed by deprotection of the alcohol to provide compound K.

The alternative approach to compound K involves similar steps, but in a different order, as shown in scheme 3:

Scheme 3

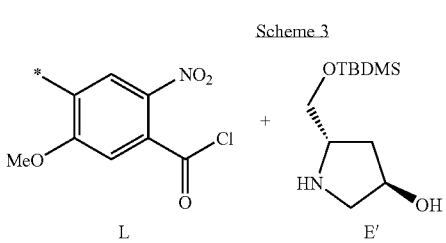
L     E'

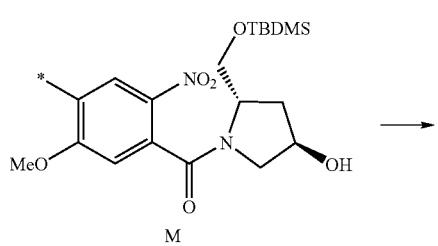
M

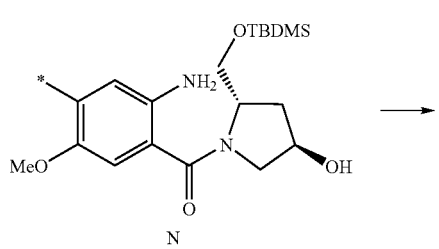
N

-continued

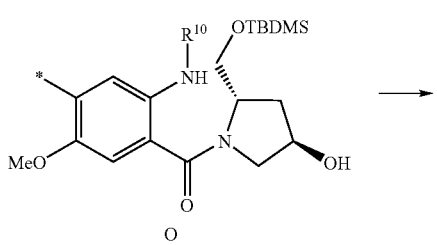
O

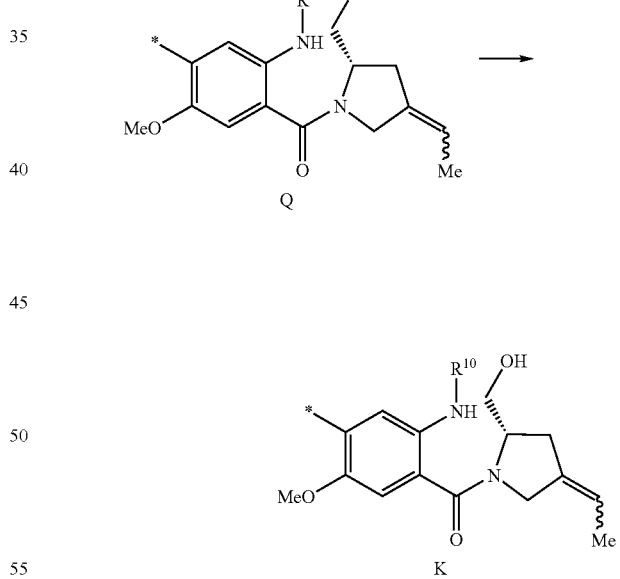

The nitro dimer M is synthesised by coupling the amine E' to the dimeric acid chloride L. The nitro dimer is then converted to the protected aniline O via the aniline N, by reduction and then protection. The hydroxy group in the C ring can then be converted to the ketone (P) and subsequently ethylidene (Q) as described above. The compound Q may then be deprotected on the hydroxy to yield compound K.

The compound K may then be cylclised to yield a compound of formula I, wherein R$^{11}$ is OH:

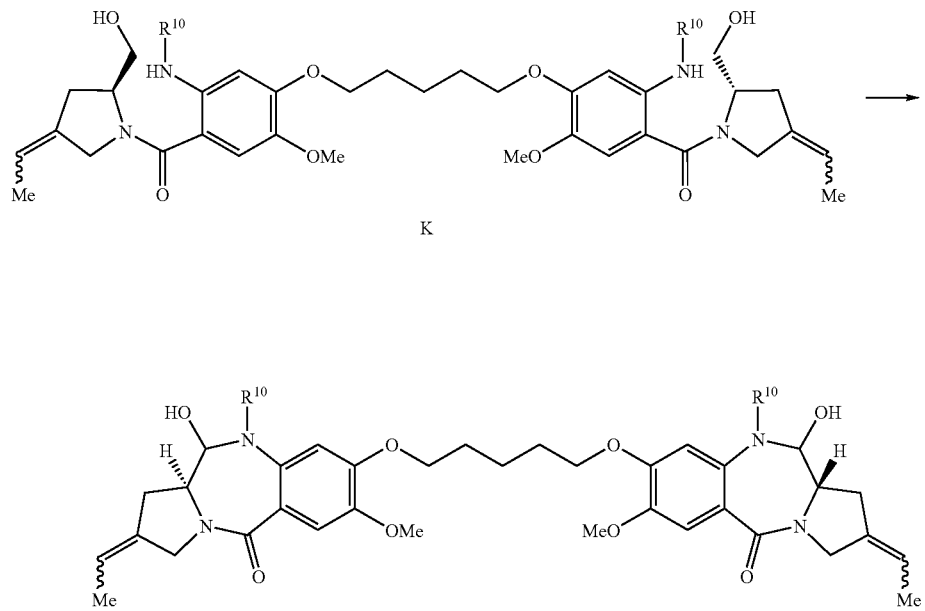

K

Exposure of the alcohol K (in which the Pro-N10-nitrogen is protected as carbamate) to tetrapropylammonium perruthenate (TPAP)/N-methylmorpholine N-oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g). A particularly preferred oxidising agent is (diacetoxyiodo)benzene (1.1 eq) and TEMPO (0.1 eq) dissolved in $CH_2Cl_2$.

Alternative methods of cylisation are illustrated in WO 00/12508.

The compound of formula I where $R^{10}$ is a nitrogen protecting group and $R^{11}$ is OH may be deprotected to a compound with N10-C11 imine bonds, by removal of the nitrogen protecting groups using appropriate conditions. If in the compound of formula I, $R^{11}$ is O—$R^{12}$, then the oxygen protecting group can be introduced using the appropriate conditions.

The relative amounts of different forms of the compound of formula I with regard to the geometry of the C2-exo double bond may be affected by the synthesis route used, and, in particular, by the Wittig reagent used.

Further Preferences

It is preferred that $R^{10}$ and $R^{11}$ together form a double bond between N10 and C11.

It is preferred that the compound of formula I comprises at least 50% in either the E-, E- or Z-, Z-forms, with more preferably at least 70%, 80%, 90% or 95% in one of these forms. The Z-, Z-form is preferred.

EXAMPLES

General Methods

Progress of reaction was monitored by thin-layer chromatography (TLC) using GF254 silica gel, with fluorescent indicator on glass plates. Visualization of TLC plates was achieved with UV light and $I_2$ vapour unless otherwise stated. Flash chromatography was performed using silica gel (14 cm column of J.T Baker 30-60 μm). The majority of reaction solvents were purified and used fresh by distillation under nitrogen from the indicated drying agent: $CH_2Cl_2$ and MeCN ($CaH_2$), tetrahydrofuran and toluene (sodium benzophenone ketyl), and MeOH (magnesium turnings and catalytic iodine). Extraction and chromatography solvents were purchased and used without further purification from J.T Baker. All organic chemicals were purchased from Aldrich Chemical Co. Drying agents and inorganic reagents were bought from BDH.

IR spectra were recorded with a Perkin-Elmer FT/IR-Paragon 1000 spectrophotometer. $^1H$ and $^{13}C$ NMR spectra were obtained on a Jeol GSX 270 MHz (67.8 MHz for $^{13}C$ NMR spectra), Brüker ARX 250 MHz (62.9 MHz for $^{13}C$ NMR spectra) or Jeol JNM-LA 400 MHz (100 MHz for $^{13}C$ NMR spectra) FT-NMR instrument operating at 20° C.±1° C. Chemical shifts are reported in parts per million (δ ppm) downfield from internal $Me_4Si$. Spin multiplicities are described as s (singlet), br s (broad singlet), d (doublet), br d (broad doublet), t (triplet), q (quartet), quint (quintet) and m (multiplet). Mass spectra were recorded on a Jeol JMS-DX 303 GC-mass spectrometer or a VG ZAB-SE double-focusing instrument.

Electron impact (EI) mass spectra were obtained at 70 eV, chemical ionisation (CI) spectra were obtained using isobutane as reagent gas, and fast atom bombardment (FAB) spectra were recorded using 3-nitrobenzyl alcohol as a matrix with Xe reagent gas. Accurate molecular masses were determined by peak matching using perfluorokerosene (PFK) as an internal standard. Optical rotations were measured at ambient temperature using a Bellingham and Stanley ADP 220 polarimeter.

Example 1

Synthesis of 1,1'-[(Pentane-1,5-diyl)dioxy]-bis[(11aS,2Z)-7-methoxy-2-ethylidene-1,2,3,11a-tetrahydro-5H-pyrrolo[2,1-c][1,4]benzodiazepin-5-one] (1)

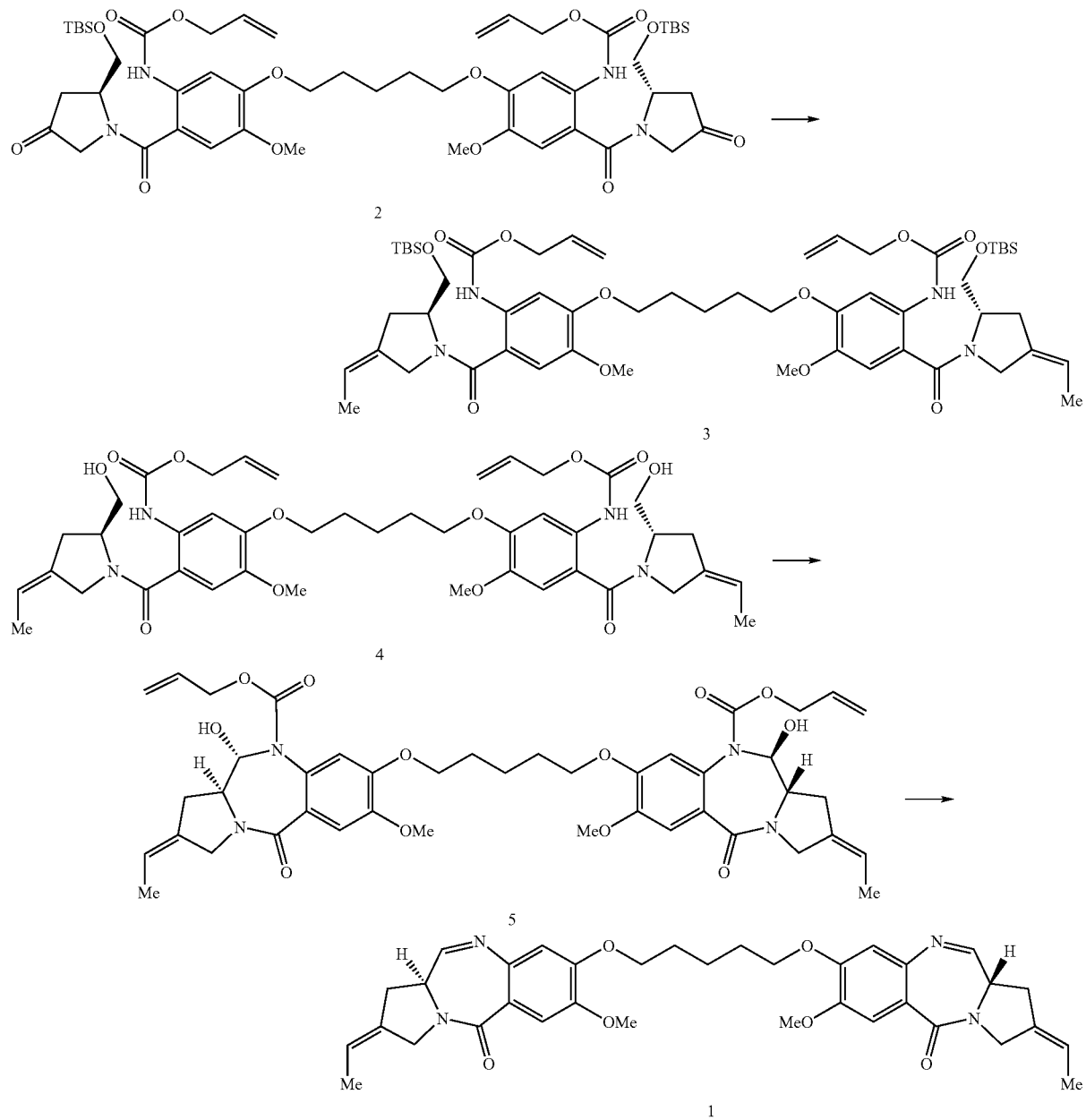

(a) 1,1'-[[(Pentane-1,5-diyl)dioxy]-bis[2-amino-N-allyloxycarbonyl-5-methoxy-1,4-phenylenecarbonyl]]-bis[(2S,4Z)-2-t-butyldimethylsilyloxymethyl-4-ethylidene-2,3-dihydropyrrole] (3)

A solution of potassium-t-butoxide in dry THF (0.5 M, 21.0 mL, 10.6 mmol) was added dropwise to a suspension of ethyltriphenylphosphonium bromide (3.94 g, 10.6 mmol) in dry THF (16 mL). The resulting yellow ylide suspension was allowed to stir at reflux for 2 hours before the addition of a solution of the bis-ketone 2 (Compound 214 from WO 00/12508) (2.09 g, 2.04 mmol) in THF (15 mL) at 10° C. The reaction mixture was allowed to stir at reflux for a further 90 minutes and then allowed to cool to room temperature. The mixture was partitioned between EtOAc (100 mL) and water (100 mL) and the organic layer was washed with sat. sodium chloride (100 mL) and dried over $MgSO_4$. Removal of excess solvent gave a brown oil that was subjected to flash column chromatography (50:50 v/v EtOAc/40-60° petroleum ether) to afford the olefin 3 as a yellow glass. Yield=577 mg (28%); $[\alpha]^{24}_D = -26°$ (c=0.453, $CHCl_3$); $^1H$ NMR (250 MHz, $CDCl_3$) δ 8.82 (bs, 2H), 7.81 (bs, 2H), 6.84 (s, 2H), 6.02-5.87 (m, 2H), 5.38-5.20 (m, 6H), 4.63-4.55 (m, 6H), 4.15-3.85 (m, 8H), 3.82-3.52 (m, 10H), 2.75-2.49 (m, 4H), 2.03-1.80 (m, 4H), 1.77-1.22 (m, 8H), 0.85 (s, 18H), 0.00 (s, 12H); $^{13}$C NMR (62.9 MHz, CDCl$_3$) δ 168.9, 153.5, 150.6 143.9 135.6 132.6, 131.9 118.0, 116.7, 115.4, 111.3, 105.4, 68.6, 65.7, 63.7, 56.6, 54.6, 33.4, 28.8, 25.8, 22.6, 18.1, 14.6, −5.58; MS (FAB) m/z (relative intensity) 1072 ([M+Na+H]$^+$, 65), 1049 ([M+H]$^+$, 28), 992 (13), 809 (39), 509 (33), 469 (49), 318 (26), 268 (100); IR (Neat) 3319 (br), 2952, 2930, 2858, 1732, 1600, 1524, 1470, 1407, 1360, 1331, 1258, 1202, 1115, 1052, 1027, 938, 837, 812, 666 cm$^{-1}$; HRMS [M+Na]$^+$ calcd for C$_{55}$H$_{84}$N$_4$O$_{12}$Si$_2$Na m/z 1071.5522, found (FAB) m/z 1071.5468.

(b) 1,1'-[[(Pentane-1,5-diyl)dioxy]-bis[2-amino-N-allyloxycarbonyl-5-methoxy-1,4-phenylenecarbonyl]]-bis[(2S,4Z)-2-hydroxymethyl-4-ethylidene-2,3-dihydropyrrole] (4)

A solution of TBAF (3.00 mL of a 1.0 M solution in THF, 3.00 mmol) was added to the bis-silyl ether 3 (1.23 g, 1.21 mmol) in THF (30 mL) at 0° C. (ice/acetone). The reaction mixture was allowed to warm to room temperature and to stir overnight, the following day, TLC (50:50 v/v EtOAc/40-60° petroleum ether) revealed the complete disappearance of starting material. Saturated NH$_4$Cl (150 mL) was added and the reaction mixture extracted with EtOAc (3×60 mL), washed with sat. sodium chloride (150 mL), dried (MgSO$_4$), filtered and evaporated in vacuo to give a yellow oil. Purification by flash chromatography (97:3 v/v CHCl$_3$/MeOH) provided the pure alcohol 4 as a white foam. Yield=879 mg (91%); [α]$^{23}_D$=−2° (c=0.29, CHCl$_3$); $^1$H NMR (250 MHz, CDCl$_3$) δ 8.64 (bs, 2H), 7.58 (bs, 2H), 6.82 (bs, 2H), 6.04-5.88 (m, 2H), 5.41-5.21 (m, 6H), 4.71-4.56 (m, 6H), 4.12-3.60 (m, 20H), 2.72 (dd, 2H, J=8.2, 15.1 Hz), 2.38 (d, 2H, J=15.3 Hz), 2.00-1.89 (m, 4H), 1.75-1.50 (m, 8H); $^{13}$C NMR (62.9 MHz, CDCl$_3$) δ 170.5, 153.7, 150.4, 144.5, 134.2, 132.6, 130.9, 118.0 (×2), 116.2, 110.9, 106.0, 68.5, 65.7, 65.3, 59.4, 56.6, 51.0, 34.1, 28.6, 22.7, 14.6; MS (FAB) m/z (relative intensity) 843 ([M+Na]$^+$, 100), 821 ([M+H]$^+$, 17), 694 (32), 509 (43), 469 (40), 421 (25), 336 (50), 307 (34); IR (CHCl$_3$) 3355 (br), 3016, 2941, 2875, 1723, 1600, 1525, 1465, 1434, 1409, 1330, 1266, 1216, 1179, 1118, 1072, 1051, 1028, 995, 933, 872, 667 cm$^{-1}$; HRMS [M+Na]$^+$ calcd for C$_{43}$H$_{56}$N$_4$O$_{12}$Na m/z 843.3792, found (FAB) m/z 843.3823.

(c) 1,1'-[(Pentane-1,5-diyl)dioxy]-bis[(11S,11aS,2Z)-10-(allyloxycarbonyl)-11-hydroxy-7-methoxy-2-ethylidene-1,2,3,10,11,11a-hexahydro-5H-pyrrolo[2,1-c][1,4]benzodiazepin-5-one] (5)

A solution of dimethyl sulphoxide (0.45 g, 0.41 mL, 5.80 mmol) in dry CH$_2$Cl$_2$ (8 mL) was added dropwise, over a 15 minute period, to a stirred solution of oxalyl chloride (1.46 mL of a 2M solution in CH$_2$Cl$_2$, 2.92 mmol) at −45° C. under a nitrogen atmosphere. The reaction mixture was allowed to stir for 35 minutes at −45° C. followed by addition of the diol 4 (0.85 g, 1.04 mmol) in CH$_2$Cl$_2$ (8 mL) at the same temperature over 15 minutes. After a further 45 minutes a solution of triethylamine (0.83 g, 1.14 mL, 8.20 mmol) in CH$_2$Cl$_2$ (8 mL) was added over a period of 15 minutes. The reaction mixture was allowed to stir at −45° C. for 30 minutes before being allowed to warm to room temperature over 45 minutes. The reaction mixture was diluted with CH$_2$Cl$_2$ and was washed with 1M HCl (3×50 mL), brine (50 mL) and dried over MgSO$_4$. Removal of excess solvent yielded the crude product, which was purified by flash column chromatography (99:1 v/v CHCl$_3$/MeOH) to afford the product as a white glass 5. Yield=0.495 g (58%); [α]$^{22}_D$=+168° (c=0.28, CHCl$_3$); $^1$H NMR (400 MHz, CDCl$_3$) δ 7.23 (s, 2H), 6.66 (s, 2H), 5.90-5.70 (m, 2H), 5.59-5.40 (m, 4H), 5.16 (bs, 2H), 5.11 (bs, 2H), 4.66 (dd, 2H, J=5.57, 13.59 Hz), 4.44 (d, 2H, J=13.2 Hz), 4.29-4.07 (m, 6H), 4.01 (t, 4H, J=6.5 Hz), 3.90 (s, 6H), 3.63-3.56 (m, 2H), 2.93-2.77 (m, 2H), 2.66 (d, 2H, J=16.4 Hz), 1.97-1.86 (m, 4H), 1.68-1.61 (m, 8H); $^{13}$C NMR (62.9 MHz, CDCl$_3$) δ 166.8, 155.9, 150.2, 148.8, 133.0, 131.8, 128.4, 125.5, 119.6, 118.2, 113.9, 110.6, 85.9, 69.0, 66.8, 59.3, 56.1, 47.5, 34.8, 28.5, 22.4, 14.8; MS (FAB) m/z (relative intensity) 839 ([M+Na]$^+$, 100), 799 (10), 781 (14), 465 (14), 443 (16), 413 (37), 388 (19), 336 (25), 271 (25); IR (CHCl$_3$) 3225 (br), 3011, 2938, 2860, 1704, 1605, 1515, 1469, 1436, 1410, 1307, 1284, 1215, 1129, 1077, 1018, 994, 959, 916, 872, 666, 637 cm$^{-1}$; HRMS [M+Na]$^+$ calcd for C$_{43}$H$_{52}$N$_4$O$_{12}$Na m/z 839.3479, found (FAB) m/z 839.3497.

(d) 1,1'-[(Pentane-1,5-diyl)dioxy]-bis[(11aS,2Z)-7-methoxy-2-ethylidene-1,2,3,11a-tetrahydro-5H-pyrrolo[2,1-c][1,4]benzodiazepin-5-one] (1)

A catalytic amount of tetrakis(triphenylphosphine)palladium (14.4 mg, 12.5 μmol) was added to a stirred solution of the bis-alloc-carbinolamine 5 (200 mg, 0.25 mmol), triphenylphosphine (6.30 mg, 24.1 μmol) and pyrrolidine (33 mg, 40.1 μL 0.48 mmol) in CH$_2$Cl$_2$ (13 mL) under a nitrogen atmosphere. The reaction mixture was allowed to warm to room temperature and the progress of reaction monitored by TLC (95:5 v/v CHCl$_3$/MeOH). After two and a half hours TLC revealed the reaction was complete to give a spot which fluoresced brightly under UV light. The solvent was evaporated under reduced pressure and the resulting residue subjected to flash chromatography (98:2 v/v CHCl$_3$/MeOH) to give the bis-imine target molecule 1 as a pale orange glass which was repeatedly evaporated in vacuo with CHCl$_3$ to provide the imine form. Yield=160 mg (Quant); [α]$^{21}_D$=+937° (c=0.641, CHCl$_3$); $^1$H NMR (250 MHz, CDCl$_3$) δ 7.67 (d, 2H, J=4.5 Hz), 7.50 (s, 2H) 6.80 (s, 2H), 5.63-5.55 (m, 2H), 4.38-3.96 (m, 8H), 3.94 (s, 6H), 3.86-3.80 (m, 2H), 3.20-3.03 (m, 2H), 2.90 (d, 2H, J=15.8 Hz), 2.00-1.91 (m, 4H), 1.76-1.68 (m, 8H); $^{13}$C NMR (62.9 MHz, CDCl$_3$) δ 164.9, 163.0, 150.8, 147.8, 140.6, 132.9, 119.3, 111.4, 110.3, 68.7, 56.1, 53.4, 48.3, 35.3, 28.6, 22.5, 14.9; MS (FAB) m/z (relative intensity) 613 ([M+H]$^+$, 52), 443 (26), 421 (22), 329 (100), 307 (71), 242 (35), 220 (38); IR (CHCl$_3$) 3220 (br), 2940, 2859, 1697, 1602, 1560, 1508, 1458, 1432, 1382, 1341, 1263, 1217, 1132, 1098, 1065, 1007, 875, 666 cm$^{-1}$; HRMS [M+H]$^+$ calcd for C$_{35}$H$_{41}$N$_4$O$_6$ m/z 613.3026, found (FAB) m/z 613.3047.

Determination of Relative Amounts of Geometric Isomers

The chemical shift differences observed in the $^{13}$C NMR spectra for the C1 and C3 resonances of the E/Z ethylidene group of the PBD allows the determination of approximate geometric isomer ratios in compound 1. These observations are based on work published on the total synthesis of the PBD natural products tomaymycin and prothracarcin which contain C2-ethylidene moieties (Mori, M., et al., *Tetrahedron*, 42, 3793 (1986)).

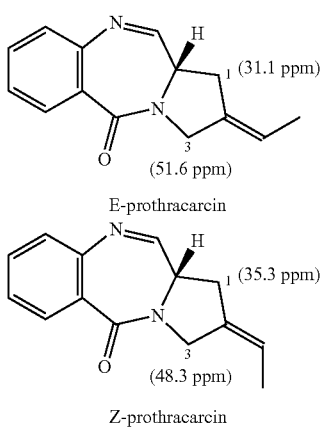

E-prothracarcin

Z-prothracarcin

Table 1 shows a comparison of $^{13}$C NMR signals for C1 and C3 of E- and Z-prothracarcin and E/Z forms of the C2-exo double bond of Compound 1. The relative signal intensities measured for Compound 1 are quoted in parentheses.

TABLE 1

| | Chemical Shift (ppm) | | | |
|---|---|---|---|---|
| | E-prothracarcin | Z-prothracarcin | E-1 | Z-1 |
| C1 | 31.1 | 35.3 | 31.1 (0.21) | 35.3 (2.60) |
| C3 | 51.6 | 48.3 | 51.6 (0.20) | 48.3 (2.84) |

From these data the approximate amount of C2 exo double bond in the Z- form is 93.6% and in the E-form is 6.4% which give the relative amounts of geometric isomers of compound 1 as below:

| Geometric isomers at C2/C2' | Amount (%) |
|---|---|
| E-, E- | 0.4 |
| E-, Z- | 12 |
| Z-, Z- | 87.6 |

In addition, NOESY (through space correlations) spectra on compound 1 supports the structural assignment.

Example 2

Biological Evaluation

K562 Assay

K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of the test compound for 1 hour at 37° C. in the dark. The incubation was terminated by centrifugation (5 minutes, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$.

The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 µL of MTT solution (5 mg/mL in phosphate-buffered saline) was added to each well and the plates further incubated for 5 hours. The plates were then centrifuged for 5 minutes at 300 g and the bulk of the medium pipetted from the cell pellet leaving 10-20 µL per well. DMSO (200 µL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

The $IC_{50}$ value measured for compound 1 was >0.05 nM, which compares to a value for the compound of Example 6 in WO 93/18045 quoted as 10 nM.

DNA Cross-Linking Assay

The extent of DNA cross-linking induced by the test compound was determined using the electrophoretic assay method of Hartley and co-workers (Hartley, J. A., et al., *Analytical Biochemistry*, 193, 131-134 (1991)). Closed-circular puc18 DNA was linearized with HindIII, then dephosphorylated and finally 5'-singly end-labelled using [$\gamma^{32}$P]-ATP and polynucleotide kinase. Reactions containing 30-40 ng of DNA were carried out in aqueous TEOA (25 mM triethanolamine, 1 mM EDTA, pH 7.2) buffer at 37° C. in a final volume of 50 µL. Reactions were terminated by addition of an equal volume of stop solution (0.6 M NaOAc, 20 mM EDTA, 100 µg/mL tRNA) followed by precipitation with EtOH. Following centrifugation, the supernatant was discarded and the pellet dried by lyophilization. Samples were re-suspended in 10 µL of strand separation buffer (30% DMSO, 1 mM EDTA, 0.04% bromophenol blue and 0.04% xylenecyanol) and denatured by heating to 90° C. for 2.5 minutes, followed by immersion in an ice/water bath. Control, non-denatured, samples were re-suspended in 10 µL of non-denaturing buffer solution (0.6% sucrose, 0.04% bromophenol blue in aqueous TAE buffer [40 mM Tris, 20 mM acetic acid, 2 mM EDTA, pH 8.1]) and loaded directly onto the gel for comparison. Electrophoresis was carried out for 14-16 h at 40 V using a 0.8% submerged agarose gel (20×25× 0.5 cm) in TAE buffer. Gels were dried under vacuum for 2 hours at 80° C. onto one layer each of Whatman 3MM and DE81 filter papers using a BioRad 583 gel dryer. Autoradiographs were obtained after exposure of Hyperfilm-MP film (Amersham plc, U.K.) to the dried gel for either 4 h with a screen, or overnight without a screen (to obtain a sharper image). Film bands were quantitated using a BioRad GS-670 imaging laser densitometer. Percentage cross-linking was calculated by measuring the total DNA in each lane (summed density for the double-stranded [DS] and single-stranded [SS] bands) relative to the amount of cross-linked DNA (density of DS band alone). A dose-response curve was derived by plotting drug concentration against the determined percentage level of cross-linked DNA, and the result $XL_{50}$ determined as the amount required to cross-link 50%.

The $XL_{50}$ determined for compound 1 was 2.7±1.6 nM.

Example 3

Antibacterial Evaluation

Materials and Methods

Collections

The MRSA collection held by Dr P. Taylor, School of Pharmacy, London (UK) was used to evaluate compound 1. It comprises 38 strains includes many international strains, as the epidemic EMRSA-15 and EMRSA-16, responsible in many outbreaks in UK hospitals for the last decade. The countries of origin of these strains is shown in table 2.

TABLE 2

| Country of Origin | Strain No. |
| --- | --- |
| Australia | Aus K, Aus D, Aus 5, Aus 7 |
| Brazil | BZ16, BZ23, BZ24, BZ9, BZ20 |
| Chile | Chil 1 |
| Denmark | DEN 2, DEN 3 |
| France | F2, F4, F25 |
| Finland | FIN 12, FIN 10 |
| Germany | G13, G1, G2, G3, G14, EG6 |
| Greece | AT5, AT6 |
| Hong Kong | HK 1 |
| India | Ind3 |
| Israel | IS 1 |
| Poland | POL2, POL3 |
| Portugal | P1, P3 |
| Kuwait | KW7 |
| South Carolina | SC4 |
| Turkey | T7 |
| United Kingdom | EMRSA15, EMRSA16 |

VRE and the remaining strains used are also held by Dr P. Taylor and are from UK collections. The following number of clinical isolates were used—20 VRE, 12 *Streptococcus pyogenes*, 12 *Streptococcus agalactiae*, 12 *Listeria monocytogenes*.

MICs (Maximum Inhibitory Concentrations)

Broth MICs were performed according to the method given by the National Committee for Clinical Laboratory Standards, UK (NCCLS) guidelines. 100 µl of the compound to be tested, suspended in Muller Hinton Broth (MHB), was dispensed in a sterile 96 well microtitre plate at the desired concentrations. One row of wells contained only 100 µl of MHB, without compound, to be used as a control. Bacterial cultures grown overnight in 2 ml of MHB were diluted down, prior to adding 100 µl of each sample to the wells, in order to obtain a final bacterial count of $5\times10^5$ CFU/ml, i.e. $10^5$ CFU per well. A final volume of 200 µl per well was obtained. A lin2 dilution of the bacterial sample, achieved once the sample was added to the well, must be taken into consideration when calculating the final bacterial count. An adhesive plastic seal was used to seal off the microtitre plate, which was then gently shaken in order to suspend the bacterial samples evenly. The plate was incubated overnight at 37° C. The lowest concentration at which there was no visible growth of bacteria is defined as the MIC for that particular bacterial strain.

The test was valid if there was evidence of bacterial growth in the control set of wells. Bacterial growth is usually represented by buttons or clumps at the bottom of the well, however some wells may appear turbid. A clear well indicates inhibition of growth.

The average count of Gram-positive bacterial culture was $10^9$ bacteria/ml which was taken into consideration when bacterial dilutions were performed prior to proceeding with the MIC test. Viable counts from the diluted bacterial suspensions were performed in order to confirm that the right final bacterial count has been achieved.

Antimicrobial Susceptibility Tests

These were performed in accordance with the NCCLS guidelines, Sixth edition, January 1997.

Several bacterial colonies were transferred from the agar plates to bijoux containing MHB. The suspension is incubated at 35° C. and subsequently diluted down in sterile saline to match the density of a McFarland standard solution. A sterile cotton swab is then dipped in the bacterial inoculum and pressed against the bijou walls to remove any excess solution. MHA plates are then thoroughly streaked with the swab three times, turning the plate 60° each time. The discs are placed onto the inoculated plate within 15 minutes. The positions of the discs should allow enough space (≈24 mm) around each individual disc in order to measure the diffusion diameter at a later stage. The plates were incubated immediately at 35° C. for 16-18 hours for all organisms excluding VRE, and MRSA, which require a 24-hour incubation. The experiment was valid if there was a confluent bacterial growth, not single colonies, and circular inhibition zones were evident. Clear zones produced around the disc were measured with a ruler and interpreted according to the tables provided by the NCCLS. Bacteria were classified as sensitive, intermediate or resistant.

Time-Kill Studies 250 ml flasks containing 50 ml of MHB were sterilised. One was kept as control, while the compound to be tested was added to the remaining three in an increasing concentration as follows: MIC×1, MIC×2 and MIC×4. An overnight bacterial culture was diluted one in two. 50 ml of that suspension were added to each flask and the time noted as time 0. Samples of each flask were taken out immediately and dispensed in bijou bottles. 100 µl of each sample were transferred to 900 µl of sterile PBS. Further 10-fold dilutions were carried out as necessary. 20 µl drops of each dilution were plated out onto NA plates and incubated overnight at 37° C. The flasks were left on a shaker at 37° C. The same procedure was repeated at time 1, 2, 4, 6 and 24 h and plates were incubated overnight.

Bacterial colonies were counted the next day. Once it was established at what dilution, number of colonies was countable the experiment was repeated, however instead of plating out 20 µl drops, 100 µl of the corresponding dilutions were spread onto a whole plate using a sterile glass rod. This enables more accurate bacterial count of the primary suspension in the flask.

Results

MICs

The average MICs for compound 1 against the collections of bacteria tested are shown in Table 3.

TABLE 3

| | $MIC_{90}$ µg/ml (mg/L) |
| --- | --- |
| MRSA | 0.03 |
| VRE | 0.06 |
| *Streptococcus pyogenes* | 0.015 |
| *Streptococcus agalactiae* | 0.015 |
| *Listeria monoocytogenes* | 0.06 |

The MICs observed in MRSA against the recently introduced antibiotics linezolid and synercid are in the range of 1 mg/L and 0.5 mg/L respectively (Munoz Bellido, J. L., et al., *International Journal of Antimicrobial Agents*, 20, 61-64 (2002); Abb, J., *Diagnostic Microbiology and Infectious Disease*, 43, 319-321 (2002)). The MIC for vancomycin against MRSA is about 2 mg/L.

Figure 2:
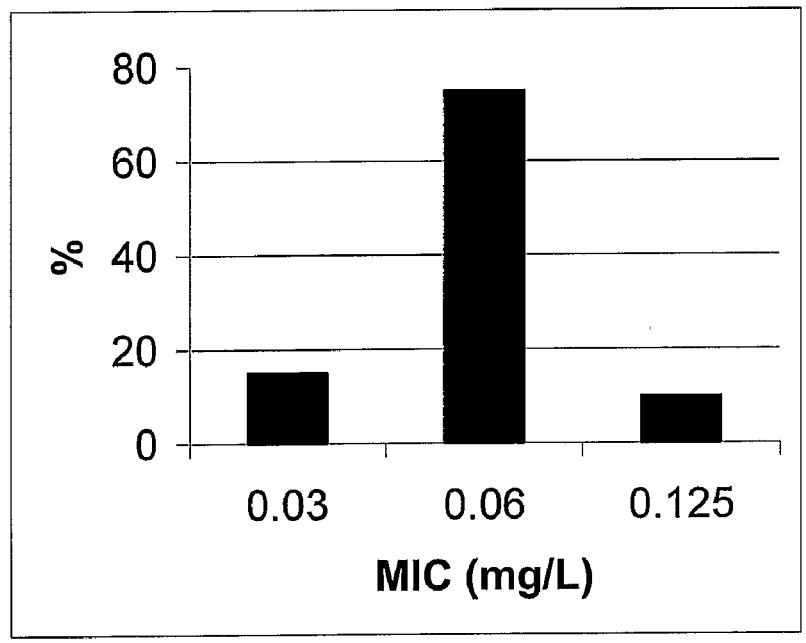
FIG. 2 shows the distribution of MICs of different VRE strains for compound 1.

FIG. 1 shows the distribution of MICs for the different strains of MRSA tested and FIG. 2 shows the distribution of MICs for the different strains of VRE tested.

Antibiotic Susceptibility Testing

The bacteria used to assess the antibacterial activity of compound 1 were tested against a wide range of antibiotics to determine their overall susceptibility to other antimicrobial agents, and the results are shown in tables 4 to 8 below.

TABLE 4

MRSA susceptibility to current antibiotics.

| | Resistant % | Sensitive % | Intermediate % |
|---|---|---|---|
| Oxacillin | 100 | — | — |
| Vancomycin | — | 100 | — |
| Trimethophrim | 32 | 68 | — |
| Amikacin | 16 | 73 | 11 |
| Gentamicin | 70 | 22 | 8 |
| Tetracycline | 84 | 16 | — |
| Rifampicin | 11 | 81 | 8 |
| Ciprofloxacin | 11 | 89 | — |
| Erythromycin | 11 | 89 | — |
| Clindamycin | 41 | 59 | — |

TABLE 5

VRE susceptibility to current antibiotics.

| | Resistant % | Sensitive % | Intermediate % |
|---|---|---|---|
| Oxacillin | 100 | — | — |
| Vancomycin | 100 | — | — |
| Trimethophrim | 75 | 25 | — |
| Amikacin | | | |
| Gentamicin | 80 | 20 | — |
| Tetracycline | 60 | 40 | — |
| Rifampicin | | | |
| Ciprofloxacin | 50 | 20 | 30 |
| Erythromycin | 90 | 10 | — |
| Clindamycin | 85 | 15 | — |

TABLE 6

*Streptococcus pyogenes* susceptibility to current antibiotics.

| | Resistant % | Sensitive % | Intermediate % |
|---|---|---|---|
| Oxacillin | — | 100 | — |
| Vancomycin | — | 100 | — |
| Trimethophrim | — | 100 | — |
| Amikacin | 100 | — | — |
| Gentamicin | — | 100 | — |
| Tetracycline | — | 100 | — |
| Rifampicin | — | 100 | — |
| Ciprofloxacin | — | 100 | — |
| Erythromycin | — | 100 | — |
| Clindamycin | — | 100 | — |

TABLE 7

*Streptococcus agalactiae* susceptibility to current antibiotics.

| | Resistant % | Sensitive % | Intermediate % |
|---|---|---|---|
| Oxacillin | — | 100 | — |
| Vancomycin | — | 100 | — |
| Trimethophrim | — | 100 | — |
| Amikacin | 100 | — | — |
| Gentamicin | 100 | — | — |
| Tetracycline | 90 | 10 | — |
| Rifampicin | — | 100 | — |
| Ciprofloxacin | — | 100 | — |
| Erythromycin | — | 100 | — |
| Clindamycin | — | 100 | — |

TABLE 8

*Listeria monocytogenes* susceptibility to current antibiotics.

| | Resistant % | Sensitive % | Intermediate % |
|---|---|---|---|
| Oxacillin | 100 | — | — |
| Vancomycin | — | 100 | — |
| Trimethophrim | — | 100 | — |
| Amikacin | — | 100 | — |
| Gentamicin | — | 100 | — |
| Tetracycline | — | 100 | — |
| Rifampicin | — | 100 | — |
| Ciprofloxacin | — | 100 | — |
| Erythromycin | — | 100 | — |
| Clindamycin | 100 | — | — |

As shown in Table 4, all the MRSA strains used are still completely susceptible to vancomycin. However, vancomycin intermediate and resistant strains are now emerging (Hiramatsu, K., *American Journal of Medicine*, 104(5A), 7S-10S (1998); Quirk, M., *The Lancet infectious diseases*, 2, 510 (2002)). There is no other antibiotic which is completely active against all strains.

Time-Kill Studies

The MRSA strain P1 was chosen to investigate the bactericidal and bacteriostatic activity of compound 1. The MIC value for this particular strain represented the MIC values obtained for the majority of the strains tested (0.015 mg/L).

Figure 3A:
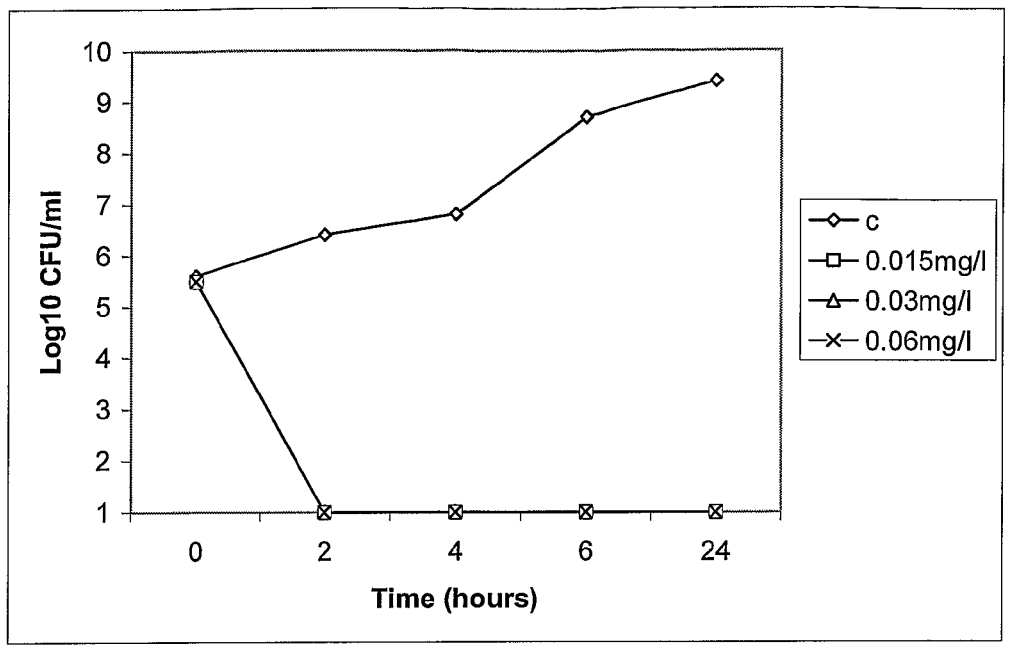
FIGS. 3*a* and 3*b* show the antibacterial activity of compound 1 on MRSA strain P1 at different time points, where the bacterial counts were calculated from 20 μL drops and 100 μL drops of the bacterial suspensions respectively.
Figure 3B:
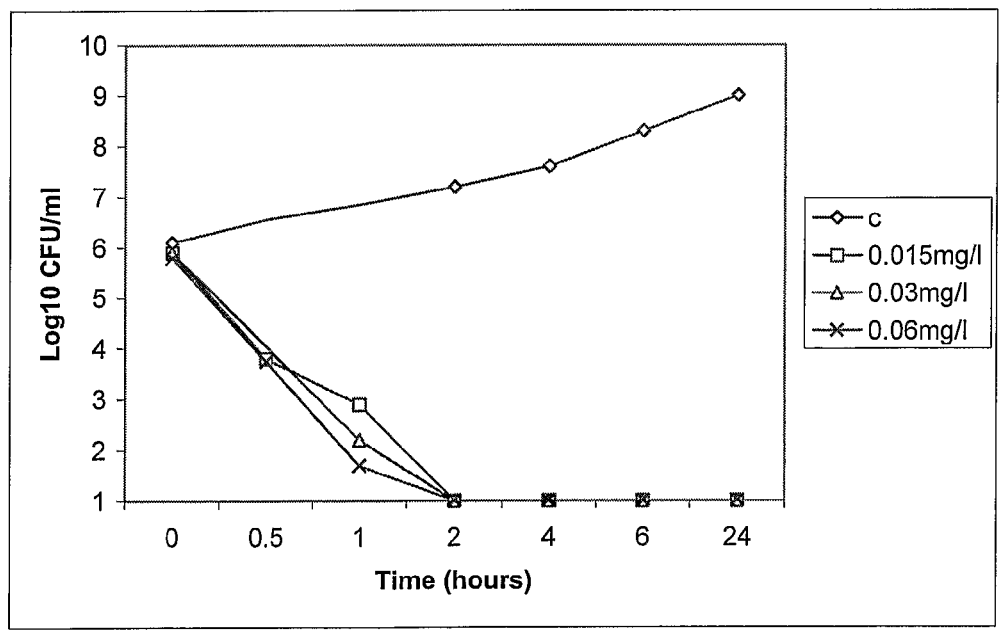

Samples of the bacterial solution with ELB-21 (20 μl drops, FIG. 3a) demonstrated that at 2 hours there was no viable bacterial growth on the agar plates. Bacterial killing seemed to occur very rapidly and a second experiment measuring bacterial counts at time 0.5 and 1 hours was performed (FIG. 3b). As indicated in the figure, after 1 hour, the bacterial counts from the MIC×1 flask (0.015 mg/l) were reduced to 1000 giving an approximate 3-log kill. It is generally accepted that a 3-log kill confirms bactericidal activity.

The remaining flasks with higher concentrations displayed even lower bacterial counts as would be expected. After two hours there was no bacterial growth observed from any of the flask samples, the data has not been plotted on the graphs, as the number of colonies is 0.

The invention claimed is:

1. A compound of formula I:

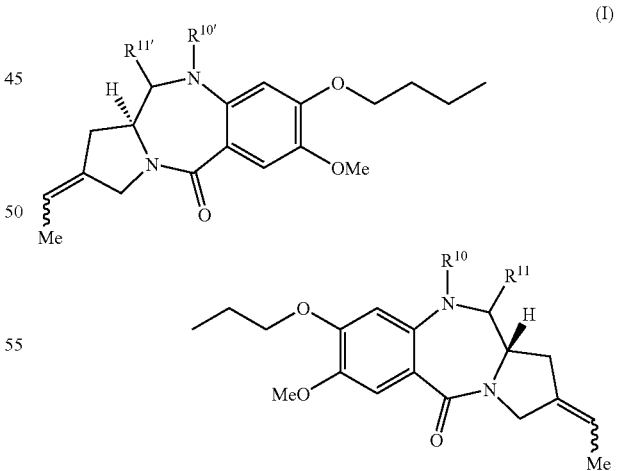

or a pharmaceutically acceptable salt thereof, wherein:
$R^{10}$ and $R^{11}$ together form a double bond between N10 and C11 or wherein $R^{10}$ is H and $R^{11}$ is OH or ORA, RA being $C_{1-7}$alkyl;
and $R^{10'}$ and $R^{11'}$ are selected from the same options as $R^{10}$ and $R^{11}$ respectively.

2. A compound of formula I:

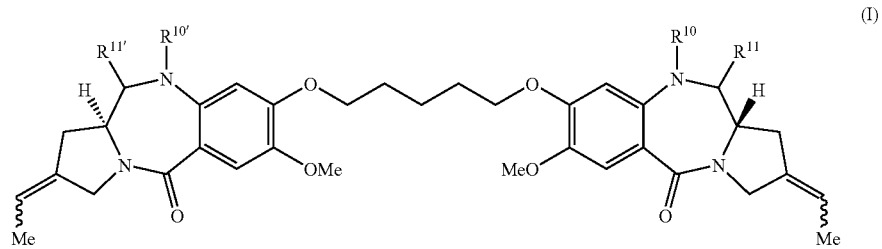

wherein:

$R^{10}$ is a nitrogen protecting group and $R^{11}$ is either OH or O—$R^{12}$, wherein $R^{12}$ is an oxygen protecting group;

and $R^{10'}$ and $R^{11'}$ are selected from the same options as $R^{10}$ and $R^{11}$ respectively.

3. A compound according to claim 2, wherein the compounds have the following stereochemistry at the C11 position:

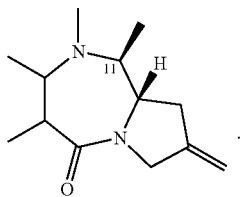

4. A compound according to claim 2, wherein the nitrogen protecting groups are selected from carbamate nitrogen protecting groups.

5. A compound according to claim 4, wherein the nitrogen protecting groups are selected from the group consisting of Alloc, Troc, Teoc, BOC, Doc, Hoc, TcBOC, Fmoc, 1-Adoc and 2-Adoc.

6. A compound according to claim 1, wherein at least 50% is in either the E-, E- or Z-, Z-forms.

7. A pharmaceutical composition comprising a compound of claim 1 or a pharmaceutically acceptable salt thereof, and a pharmaceutically acceptable excipient.

8. A method for the treatment of an infection, comprising administering to a subject suffering from an infection a therapeutically-effective amount of a compound of claim 1 or a pharmaceutically acceptable salt thereof, wherein the infection is by gram-positive bacteria.

9. The method of claim 8, wherein the gram-positive bacteria is selected from MRSA and VRE.

* * * * *